(12) United States Patent
Hotelling et al.

(10) Patent No.: US 11,009,390 B2
(45) Date of Patent: May 18, 2021

(54) METHODS AND SYSTEMS FOR MODULATION AND DEMODULATION OF OPTICAL SIGNALS

(71) Applicant: Apple Inc., Cupertino, CA (US)

(72) Inventors: Steven P. Hotelling, Los Gatos, CA (US); Marcelo M. Lamego, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 428 days.

(21) Appl. No.: 15/960,507

(22) Filed: Apr. 23, 2018

(65) Prior Publication Data

US 2018/0238734 A1 Aug. 23, 2018

Related U.S. Application Data

(63) Continuation of application No. 14/618,664, filed on Feb. 10, 2015, now Pat. No. 9,952,095.

(60) Provisional application No. 62/057,089, filed on Sep. 29, 2014.

(51) Int. Cl.
| | |
|---|---|
| *G01J 1/44* | (2006.01) |
| *A61B 5/024* | (2006.01) |
| *G01J 1/18* | (2006.01) |
| *A61B 5/00* | (2006.01) |

(Continued)

(52) U.S. Cl.
CPC ............ *G01J 1/44* (2013.01); *A61B 5/02427* (2013.01); *A61B 5/7225* (2013.01); *A61B 5/7228* (2013.01); *G01J 1/0228* (2013.01); *G01J 1/18* (2013.01); *G01J 2001/0257* (2013.01); *G01J 2001/4242* (2013.01); *G01J 2001/444* (2013.01)

(58) Field of Classification Search
CPC ............ G01J 1/0228; G01J 2001/0257; G01J 2001/4242; G01J 2001/444; A61B 5/7225; A61B 5/02427
See application file for complete search history.

(56) References Cited

U.S. PATENT DOCUMENTS

| | | |
|---|---|---|
| 4,729,128 A | 3/1988 | Grimes |
| 5,162,618 A | 11/1992 | Knowles |
| 5,381,696 A | 1/1995 | Ichinose et al. |

(Continued)

FOREIGN PATENT DOCUMENTS

| | | |
|---|---|---|
| WO | WO 94/002911 | 2/1994 |
| WO | WO 05/103872 | 11/2005 |

OTHER PUBLICATIONS

Bicz et al., "Ultrasonic sensor for fingerprints recognition," Proceedings of SPIE 2634, Optoelectgronic and Electronic Sensors, Jun. 30, 1995, doi: 10-1117/12.213142, 9 pages.

(Continued)

*Primary Examiner* — Tony Ko
(74) *Attorney, Agent, or Firm* — Brownstein Hyatt Farber Schreck, LLP

(57) ABSTRACT

An electronic device includes one or more light sources for emitting light toward a body part of a user and one or more optical sensors for capturing light samples while each light source is turned on and for capturing dark samples while the light source(s) are turned off. A signal produced by the one or more optical sensors is filtered and demodulated produce multiple demodulated signals each associated with a light source. Each signal associated with the light source(s) is analyzed to estimate or determine a physiological parameter of the user.

19 Claims, 7 Drawing Sheets

(51) Int. Cl.
*G01J 1/02* (2006.01)
*G01J 1/42* (2006.01)

(56) References Cited

U.S. PATENT DOCUMENTS

| | | | |
|---|---|---|---|
| 5,515,298 A | 5/1996 | Bicz | |
| 5,589,636 A | 12/1996 | Bicz | |
| 5,719,950 A | 2/1998 | Osten | |
| 5,886,452 A | 3/1999 | Toda | |
| 6,091,406 A | 7/2000 | Kambara | |
| 6,159,149 A | 12/2000 | Erikson | |
| 6,164,135 A | 12/2000 | Bicz | |
| 6,720,712 B2 | 4/2004 | Scott | |
| 7,032,454 B2 | 4/2006 | Amano | |
| 7,400,750 B2 | 7/2008 | Nam | |
| 7,449,821 B2 | 11/2008 | Dausch | |
| 7,458,268 B2 | 12/2008 | Schneider et al. | |
| 7,497,120 B2 | 3/2009 | Schneider et al. | |
| 7,568,391 B2 | 8/2009 | Schneider et al. | |
| 7,656,932 B2 | 2/2010 | Durand | |
| 7,667,374 B2 | 2/2010 | Aono et al. | |
| 7,734,435 B2 | 6/2010 | Thomas et al. | |
| 7,739,912 B2 | 6/2010 | Schneider et al. | |
| 7,770,456 B2 | 8/2010 | Stevenson et al. | |
| 8,047,995 B2 | 11/2011 | Wakabayashi et al. | |
| 8,054,203 B2 | 11/2011 | Breed et al. | |
| 8,085,998 B2 | 12/2011 | Setlak et al. | |
| 8,095,328 B2 | 1/2012 | Thomas et al. | |
| 8,179,678 B2 | 5/2012 | Yamashita et al. | |
| 8,201,739 B2 | 6/2012 | Schneider et al. | |
| 8,335,356 B2 | 12/2012 | Schmitt | |
| 8,345,508 B2 | 1/2013 | Wodnicki et al. | |
| 8,508,103 B2 | 8/2013 | Schmitt et al. | |
| 8,536,465 B2 | 9/2013 | Hagiwara et al. | |
| 8,576,202 B2 | 11/2013 | Tanaka et al. | |
| 8,601,876 B2 | 12/2013 | Schneider et al. | |
| 8,617,078 B2 | 12/2013 | Machida et al. | |
| 8,666,126 B2 | 3/2014 | Lee et al. | |
| 8,692,812 B2 | 4/2014 | Hecht | |
| 8,724,859 B2 | 5/2014 | Schneider et al. | |
| 8,743,091 B2 | 6/2014 | Bernstein | |
| 8,781,180 B2 | 7/2014 | Schneider et al. | |
| 8,791,792 B2 | 7/2014 | Benkley, III | |
| 8,982,089 B2 | 3/2015 | Lim | |
| 9,044,171 B2 | 6/2015 | Venkatraman et al. | |
| 9,056,082 B2 | 6/2015 | Liautaud et al. | |
| 9,100,034 B2 | 8/2015 | Oshima | |
| 9,132,693 B2 | 9/2015 | Klootwijk et al. | |
| 9,170,668 B2 | 10/2015 | Schneider et al. | |
| 9,201,546 B2 | 12/2015 | Son et al. | |
| 9,275,625 B2 | 3/2016 | Kim et al. | |
| 9,323,393 B2 | 4/2016 | Djordjev et al. | |
| 9,465,972 B2 | 10/2016 | Chung et al. | |
| 9,568,315 B2 | 2/2017 | Naoka, II et al. | |
| 9,582,705 B2 | 2/2017 | Du et al. | |
| 9,607,203 B1 | 3/2017 | Yazdandoost et al. | |
| 9,613,246 B1 | 4/2017 | Gozzini et al. | |
| 9,747,988 B2 | 8/2017 | Yazdandoost et al. | |
| 9,750,451 B2 | 9/2017 | Masson et al. | |
| 9,778,193 B2 | 10/2017 | Vacca | |
| 9,824,254 B1 | 11/2017 | Yazdandoost et al. | |
| 9,857,872 B2 | 1/2018 | Terlizzi et al. | |
| 9,904,836 B2 | 2/2018 | Yazdandoost et al. | |
| 9,927,926 B2 | 3/2018 | Peng | |
| 9,952,095 B1 | 4/2018 | Hotelling et al. | |
| 9,979,955 B1 | 5/2018 | Guo | |
| 9,984,271 B1 | 5/2018 | King et al. | |
| 10,198,610 B1 | 2/2019 | Yousefpor et al. | |
| 10,241,223 B2 | 3/2019 | Jin et al. | |
| 10,275,633 B1 | 4/2019 | Yousefpor et al. | |
| 10,275,638 B1 | 4/2019 | Yousefpor et al. | |
| 10,325,136 B1 | 6/2019 | Yeke Yazdandoost et al. | |
| 10,366,269 B2 | 7/2019 | Lu et al. | |
| 2003/0102777 A1 | 6/2003 | Kuniyasu et al. | |
| 2003/0109993 A1 | 6/2003 | Peat et al. | |
| 2004/0140735 A1 | 7/2004 | Scott et al. | |
| 2004/0264746 A1 | 12/2004 | Polcha | |
| 2006/0196271 A1 | 9/2006 | Jancsik et al. | |
| 2008/0142571 A1 | 6/2008 | Yokozuka et al. | |
| 2008/0175450 A1 | 7/2008 | Scott | |
| 2012/0092026 A1 | 4/2012 | Liautaud et al. | |
| 2013/0278111 A1 | 10/2013 | Sammoura et al. | |
| 2014/0070077 A1* | 3/2014 | Tsuchimoto | A61B 5/7203 250/214 A |
| 2014/0316305 A1* | 10/2014 | Venkatraman | A61B 5/681 600/595 |
| 2014/0333328 A1 | 11/2014 | Nelson et al. | |
| 2014/0352440 A1 | 12/2014 | Fennell et al. | |
| 2014/0355381 A1 | 12/2014 | Lal et al. | |
| 2014/0359757 A1 | 12/2014 | Sezan et al. | |
| 2015/0053006 A1 | 2/2015 | DeCoux et al. | |
| 2015/0192547 A1 | 7/2015 | Lee et al. | |
| 2015/0358740 A1 | 12/2015 | Tsai et al. | |
| 2016/0092714 A1 | 3/2016 | Yazdandoost et al. | |
| 2016/0117541 A1 | 4/2016 | Lu et al. | |
| 2016/0246396 A1 | 8/2016 | Dickinson et al. | |
| 2016/0350573 A1 | 12/2016 | Kitchens, II et al. | |
| 2017/0053151 A1 | 2/2017 | Yazdandoost et al. | |
| 2017/0263022 A1 | 9/2017 | Teshigawara et al. | |
| 2017/0357839 A1 | 12/2017 | Yazdandoost et al. | |

OTHER PUBLICATIONS

Gumienny et al., "Synthetic aperture acoustic microscope for evaluation of finger tip peripheral skin structure," Proceedings of SPIE, Optical Biophysics, Mar. 30, 1995, doi: 10.1117/12.205999, 5 pages.

* cited by examiner

METHODS AND SYSTEMS FOR MODULATION AND DEMODULATION OF OPTICAL SIGNALS

CROSS-REFERENCE TO RELATED APPLICATION

This application is a continuation of U.S. patent application Ser. No. 14/618,664, filed on Feb. 10, 2015, entitled "Methods and Systems for Modulation and Demodulation of Optical Signals," which claims the benefit under 35 U.S.C. § 119(e) of U.S. Provisional Patent Application No. 62/057,089, filed on Sep. 29, 2014, and entitled "Methods and Systems for Modulation and Demodulation of Optical Signals," both of which are incorporated by reference as if fully disclosed herein.

TECHNICAL FIELD

The present invention relates generally to health monitoring systems, and more particularly to health monitoring devices that include one or more optical sensors.

BACKGROUND

Health monitoring devices, such as fitness and wellness devices, may be capable of non-invasively measuring a variety of physiological characteristics of a subject via optical sensing. Such health monitoring devices can include a light source and an optical sensor.

The light source can illuminate a portion of a measurement site or even emit light that penetrates beneath the measurement site, such as into the stratum corneum of the skin or into blood vessels beneath the skin. Light from the light source may be scattered, absorbed, and/or reflected throughout the measurement site or the material forming the measurement site, such as the skin. The amount of scatter, absorption, or reflection can depend directly or indirectly on one or more physiological characteristics of the measurement site.

The optical sensor can collect light exiting the measurement site and generate electrical signals corresponding to the collected light, which may be conveyed (in the form of electrical signals) as information or data to the health monitoring device. The health monitoring device can use the optical sensor data to extrapolate, determine, derive, estimate, or measure physiological parameters of the measurement site.

In many cases, the optical sensor data may include noise associated with ambient light, surface conditions of the measurement site (e.g., cleanliness, hair, perspiration, etc.), proximity of the optical sensor and/or light source to the measurement site, and motion artifacts caused by the relative motion between the health monitoring device and the measurement site.

Furthermore, health monitoring devices often have a small form factor and are wearable by a subject for extended periods of time. The constrained proportions of such devices can limit the maximum physical size of the optical sensor and/or light source, effectively restricting the performance of both. For example, smaller light sources may emit less light and smaller optical sensors may detect less light. In addition, as the size of the optical sensor and/or light source decrease, the effects of noise increase. As a result, the accuracy, precision, and/or reliability of the physiological parameters derived from the optical sensor data can decrease with the size of many current health monitoring devices.

Accordingly, there may be a present need for an improved optical sensing system configured for use with a small form factor health monitoring device.

SUMMARY

Embodiments described herein may relate to, include, or take the form of an electronic device adapted to measures the optical characteristics, such as reflection or transmission, of a subject.

Embodiments described herein may relate to, include, or take the form of an electronic device including at least a housing with a surface adapted to be positioned proximate a measurement site of a subject, a biometric sensor positioned at least partially within the surface and including at least a plurality of light sources for emitting light toward the measurement site and an optical sensor for obtaining light exiting the measurement site. The electronic device can also include an input amplifier coupled to the output of the biometric sensor, a high pass filter coupled to the output of the input amplifier, an output amplifier coupled to the output of the high pass filter, and an analog to digital converter coupled to the output of the output amplifier.

Further embodiments described herein may relate to, include, or take the form of a sensor system including at least a plurality of light sources for emitting light toward a measurement site of a subject, an optical sensor for obtaining light exiting the measurement site, and an input amplifier coupled to the output of the biometric sensor, a high pass filter coupled to the output of the input amplifier, an output amplifier coupled to the output of the high pass filter, and an analog to digital converter coupled to the output of the output amplifier.

Additional embodiments described herein may relate to, include, or take the form of a method of optical sensing, including at least the operations of emitting light toward a measurement site of a subject, obtaining light exiting the measurement site, converting the obtained light to an electrical signal, amplifying the electrical signal to obtain an amplified signal, filtering low frequency elements from the amplified signal to obtain a filtered signal, and amplifying the filtered signal to obtain an output signal.

Other embodiments may include further including at least sampling the output signal to obtain a matrix of samples, and determining product of the matrix of samples with a demodulation matrix to obtain a demodulated matrix. Sampling the output signal to obtain a matrix of samples can include taking a first sample, taking a second sample, taking a third sample, subtracting the average of the first and third sample from the second sample to obtain an output sample, and inserting the output sample into the matrix of samples.

Other embodiments may include a configuration in which light may be emitted toward the measurement site from a plurality of light sources each with a light emitting diode, and light may be obtained exiting by an optical sensor with one of the group consisting of photodiodes, phototransistors, or optical image sensors.

BRIEF DESCRIPTION OF THE DRAWINGS

Reference will now be made to representative embodiments illustrated in the accompanying figures. It should be understood that the following descriptions are not intended to limit the disclosure to one preferred embodiment. To the contrary, each is intended to cover alternatives, modifica

The use of the same or similar reference numerals in different drawings indicates similar, related, or identical items where appropriate.

DETAILED DESCRIPTION

Figure 1A:
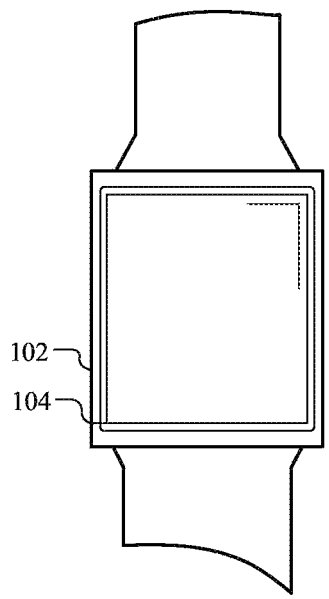
- FIG. 1A depicts a top plan view of an example health monitoring device.

Embodiments described herein relate to systems and methods for increasing the signal to noise ratio of an optical sensing system configured for use with a small form factor health monitoring device, although the various systems and methods described herein are not limited to particular form factors and can apply equally to larger embodiments. Further, it should be appreciated that the various embodiments described herein, as well as functionality, operation, components, and capabilities thereof may be combined with other elements as necessary, and so any physical, functional, or operational discussion of any element or feature is not intended to be limited solely to a particular embodiment to the exclusion of others.

Any suitable type of electronic device can include health monitoring functionality. Example electronic devices include, but are not limited to, a smart telephone, a headset, a pulse oximeter, a digital media player, a tablet computing device, a timekeeping device, a peripheral input device (e.g., keyboard, mouse, trackpad), and a wearable device. Electronic devices that include health monitoring functionality are generally referred to herein as "health monitoring devices" or "health devices" and the like. Accordingly, it is understood that a health monitoring device as described herein is not necessarily limited to devices configured to only provide health-related information, rather, a health monitoring device may include other functionality as well.

In one embodiment, one or more sensors may be included within the health monitoring device. Sensors utilized by a health monitoring device can vary from embodiment to embodiment. Suitable sensors can include temperature sensors, electrodermal sensors, blood pressure sensors, heart rate sensors, respiration rate sensors, oxygen saturation sensors, plethysmographic sensors, activity sensors, pedometers, blood glucose sensors, body weight sensors, body fat sensors, blood alcohol sensors, dietary sensors, and so on.

Certain sensors can collect certain health-related information non-invasively. For example, a health monitoring device can include a sensor that is configured to measure changes in light absorption of a measurement site of the subject. Such a sensor can be implemented as an active sensing system including a light emitter and a light detector. In one embodiment the sensing system can include a light source for emitting light into a measurement site of a subject and an optical sensor to detect light exiting the measurement site. Light from the light source may be scattered, absorbed, and/or reflected throughout the measurement sight as a function of various physiological parameters or characteristics of the subject. For example, a subject may be a human user and the measurement site may be the user's wrist. In such an example, the tissue of the user's wrist can scatter, absorb, or reflect light emitted by the light source differently depending on various physiological characteristics of the surface and subsurface of the user's wrist. In other examples, a subject can be an animal.

For example, some embodiments may be configured to detect various subsurface events, such as the user's cardiac cycle. More particularly, during each complete heartbeat, a user's subcutaneous tissue can distend and contract, alternatingly increasing and decreasing the light absorption capacity of the measurement site. In these embodiments, the optical sensor can collect light exiting the measurement site and generate electrical signals corresponding to the collected light. Thereafter, the electrical signals can be conveyed as data to the health monitoring device. One may appreciate that such a sensor is conventionally referred to as a photoplethysmographic sensor (hereinafter "PPG sensor").

As noted above, the performance optical sensors such as PPG sensors can be negatively affected by noise associated with ambient light, surface conditions of the measurement site (e.g., cleanliness, hair, perspiration, etc.), proximity of the optical sensor and/or light source to the measurement site, and motion artifacts caused by the relative motion between the health monitoring device and the measurement site. In other words, "environmental noise" can have a substantial impact on the quality of the data obtained by the optical sensor.

Accordingly, many embodiments described herein modulate the light output from the light source and demodulate the light collected by the optical sensors. In this manner, environmental noise can be at least partially prevented from interfering with the operation of the optical sensor. In many embodiments, modulation and demodulation can be implemented by toggling the light source on and off at a particular frequency. Thereafter, the optical sensor can generate electrical signals corresponding to the light collected from the measurement site. In these embodiments, the electrical signals can be demodulated and processed by the health monitoring device.

In many embodiments, the health monitoring device can implement a time-domain noise attenuation operation such as dark-channel subtraction. For example, in some embodiments, a sample can be taken from the optical sensor when it is known that the light source is not emitting light. This sample can be saved as a "dark" sample. Thereafter, a sample can be taken from the optical sensor when it is known that the light source is emitting light. Next, the dark sample can be subtracted from this "light" sample to remove the effects of noise from the light sample. In other words, a dark sample can represent an approximation of the amount of environmental noise at or near the time the dark sample was taken.

In further embodiments, a second dark sample can be taken after the light sample. In such cases, the first and second dark samples can be averaged. The averaged dark sample may be subtracted from the intervening light sample in order to remove the effects of noise from the light sample.

Although time-domain noise attenuation operations such as dark-channel subtraction may be suitable in certain embodiments for mitigating the effects of certain environmental noise sources, the delays required between "light" samples (e.g., delays where dark samples are required to be taken) can cause undesirable aliasing. In some examples, using dark-channel subtraction may require a reduction in sampling rate, which in turn can increase the number of aliases present in the data output from the optical sensor. In these examples, low frequency aliases may be particularly undesirable.

For example, many physiological signals measurable by a PPG sensor (e.g., respiration, heart rate) are relatively low frequency signals. For example, a heathy user's heart rate may vary from less than one beat per second to only a few beats per second. In other words, a heart rate may be a physiological signal within the frequency band from 0 Hz to 3-4 Hz. Accordingly, low frequency aliasing (as a result of dark-channel subtraction) can interfere with the detection and extraction of low frequency physiological signals, such as heart rate.

Accordingly, certain embodiments described herein implement a filter prior to time-domain noise attenuation. For example, a high pass or a band pass filter can be implemented to attenuate some or all frequencies except frequencies nearby the modulation frequency. In this manner, certain frequencies of environmental noise can be attenuated prior to time-domain noise attenuation operations such as dark-channel subtraction. As a result, low frequency noise sources are attenuated and, accordingly, the negative effects of low frequency aliasing can be reduced.

Although filtering prior to dark-channel subtraction may be suitable in some embodiments for attenuating certain noise sources, the process of filtering with a dynamic filter (such as a band pass or high pass filter) can increase the complexity of demodulating and/or demultiplexing the signal. For example, the time response of a dynamic filter can mix the time-multiplexed signals sent from the light source in time. In other words, dynamic filtering of a signal $S_0$ received at time $t_0$ can cause the signal $S_0$ to interfere with a signal $S_1$ sent at time $t_1$.

Accordingly, embodiments described herein relate to methods and systems for demodulating and demultiplexing signals output from an optical sensor implementing both dynamic filtering and time-domain noise attenuation.

FIG. 1A depicts a top plan view of an example health monitoring device 100. In the illustrated embodiment, the health monitoring device may be implemented as a portable electronic device that is adapted to be worn by a user. Other embodiments can implement the health monitoring device differently. For example, the health monitoring device can be a smart phone, a gaming device, a digital music player, a sports accessory device, a medical device, a device that provides time and/or weather information, a health assistant, and other types of electronic device suitable for attaching to a user.

The health monitoring device can be implemented as a wearable health assistant that provides health-related information (whether real-time or not) to the user, authorized third parties, and/or an associated monitoring device. The wearable health assistant may be configured to provide health-related information or data such as, but not limited to, heart rate data, blood pressure data, temperature data, blood oxygen saturation level data, diet/nutrition information, medical reminders, health-related tips or information, or other health-related data. The associated monitoring device may be, for example, a tablet computing device, phone, personal digital assistant, computer, and so on.

As another example, the health monitoring device can be configured in the form of a wearable communications device. The wearable communications device may include a processor coupled with or in communication with a memory, one or more sensors, one or more communication interfaces, output devices such as displays and speakers, one or more input devices, and a health monitoring system. The communication interface(s) can provide electronic communications between the communications device and any external communication network, device or platform, such as but not limited to wireless interfaces, Bluetooth interfaces, USB interfaces, Wi-Fi interfaces, TCP/IP interfaces, network communications interfaces, or any conventional communication interfaces. The wearable communications device may provide information regarding time, health, statuses or externally connected or communicating devices and/or software executing on such devices, messages, video, operating commands, and so forth (and may receive any of the foregoing from an external device), in addition to communications.

The health monitoring device 100 includes a housing 102 at least partially surrounding a display 104. In many examples, the display 104 may incorporate an input device configured to receive touch input, force input, and the like and/or output information to a user, such as various health parameters or health-related suggestions. The health monitoring device 100 may also include one or more buttons or input devices (not shown). The housing 102 can form an outer surface or partial outer surface and protective case for the internal components of the health monitoring device 100. In the illustrated embodiment, the housing 102 is formed into a substantially rectangular shape, although this configuration is not required.

The housing 102 can be formed of one or more components operably connected together, such as a front piece and a back piece or a top clamshell and a bottom clamshell. Alternatively, the housing 102 can be formed of a single piece (e.g., uniform body or unibody) operably connected to the display 104.

The display 104 can be implemented with any suitable technology, including, but not limited to, a multi-touch sensing touchscreen that uses liquid crystal display (LCD) technology, light emitting diode (LED) technology, organic light-emitting display (OLED) technology, organic electroluminescence (OEL) technology, or another type of display technology. A button (not shown) might take the form of a home button, which may be a mechanical button, a soft button (e.g., a button that does not physically move but still accepts inputs), an icon or image on the display 104 or on an input region, and so on. Other buttons or mechanisms can be used as input/output devices, such as a speaker, rotary input, a microphone, an on/off button, a mute button, or a sleep button.

Figure 1B:
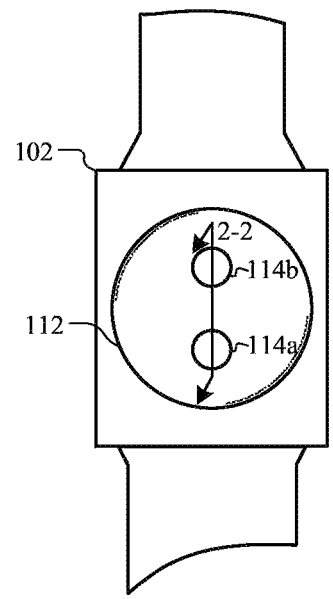
FIG. 1B depicts a bottom plan view of the health monitoring device of FIG. 1A, showing apertures associated with an optical sensing system.

The health monitoring device 100 may include one or more health sensors. In some examples, the health sensors can be disposed on a bottom surface 112 of the housing 102. For example, FIG. 1B depicts a bottom plan view of the health monitoring device of FIG. 1A, showing two apertures 114a, 114b associated with an optical sensing system that can be used to obtain health-related information from a user. As noted above, an optical sensing system can include a light source and an optical sensor (not shown). The light source can be disposed within a first aperture 114a and the optical sensor can be disposed within a second aperture 114b. In some embodiments, the light source may fill the first aperture and/or the optical sensor may fill the second aperture, while in other embodiments optically-transparent windows or covers may seal the light source and optical sensor in their respective apertures. As used herein, the term "optically transparent" and variants thereof does not necessarily mean that the structure is transparent to visible light but instead to the particular wavelength of light emitted by the light source and/or received by the sensor. Thus, some windows may pass infrared light but block visible light and still be optically transparent.

In some examples, and as illustrated, the apertures 114a, 114b the bottom surface 112 of the housing 102 may take a convex shape, although this configuration is not required. In these examples, the apertures 114a, 114b can be formed symmetrically about the apex of the convex curvature of the bottom surface 112. In this manner, the curvature of the housing itself can provide an optical barrier between the light source and the optical sensor. For example, the apex of the convex curvature of the external surface can physically and optically separate the light source from the optical sensor. In other examples, the bottom surface 112 can be flat, faceted, or concave. In further embodiments, the bottom surface 112 can take an arbitrary shape. In some embodiments, the light source and/or optical sensor may be recessed within the apertures such that there is no direct light path between the two.

The apertures 114a, 114b may be separated by a selected distance. The distance between the apertures 114a, 114b can vary from embodiment to embodiment.

Figure 2A:
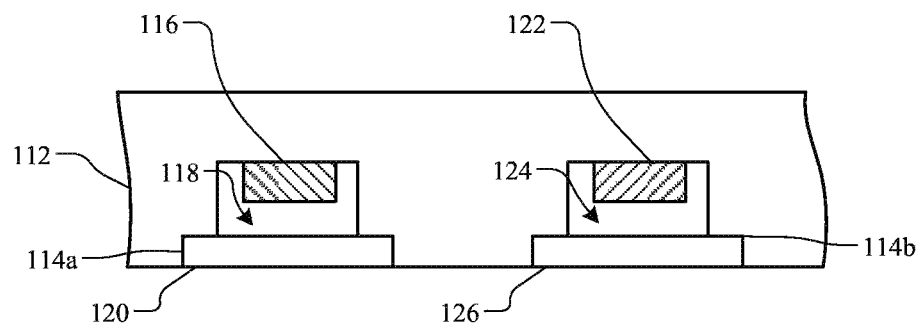
FIG. 2A depicts a detailed cross-section of FIG. 1B taken along line 2-2, showing a simplified view of the optical sensing system of FIG. 1B.

FIG. 2A depicts a detailed cross-section of FIG. 1B taken along line 2-2, showing a simplified view of the optical sensing system of FIG. 1B. The optical sensing system includes a light source 116 and an optical sensor 122. In one embodiment the light source 116 may be light emitting diode configured to emit light at a particular frequency. For example, in certain embodiments the light source 116 can be configured to emit green light. In another example, the light source 116 can emit infrared light. In still further examples, the light source 116 can be configured to emit light in another frequency band.

In many embodiments, more than one independent light source can be implemented as the light source 116. For example, certain embodiments can include four light sources within the space reserved for the light source 116. In other embodiments more or fewer light sources can be used. In these and related embodiments, the multiple individual light sources 116 can be configured to illuminate independently or at once. For example, in certain embodiments, individual light sources 116 can be illuminated in a sequence.

The optical sensor 122 can be a photodiode, phototransistor, and/or an optical image sensor such as a charge-coupled device ("CCD") or complementary metal-oxide semiconductor ("CMOS") array.

The light source 116 can be disposed within a cavity 118 that extends to the aperture 114a. In some embodiments, the cavity 118 may have a shorter width than that of the aperture 114a, although this configuration is not required.

A lens 120 or window may seal the cavity 118; the lens 120 need not focus or scatter light in any particular fashion. The lens 120 may be formed from the same material as the bottom surface 112, although this is not required. In one embodiment, the lens 120 can be configured to diffuse light, while in other embodiments it may focus light or may not affect the directionality of light passing therethrough. In some embodiments, the lens 120 may be optically transparent. In still further embodiments, the lens 120 may be configured to exhibit transparency in a first light frequency band and to be opaque in a second light frequency band. For one example, the first light frequency band can be infrared light and the second light frequency band can be visible light.

As with the light source 116, the optical sensor 122 can be disposed within a cavity 124 and below another window or lens 126. As with the lens 120, the lens 126 can be configured to diffuse light. In other embodiments, the lens 126 may be optically transparent, or may be shaped to focus light to a particular focal point (or not). In still further embodiments, the lens 126 may be configured to exhibit transparency in a first light frequency band and to be opaque in a second light frequency band. For one example, the first light frequency band can be infrared light and the second light frequency band can be visible light.

Figure 2B:
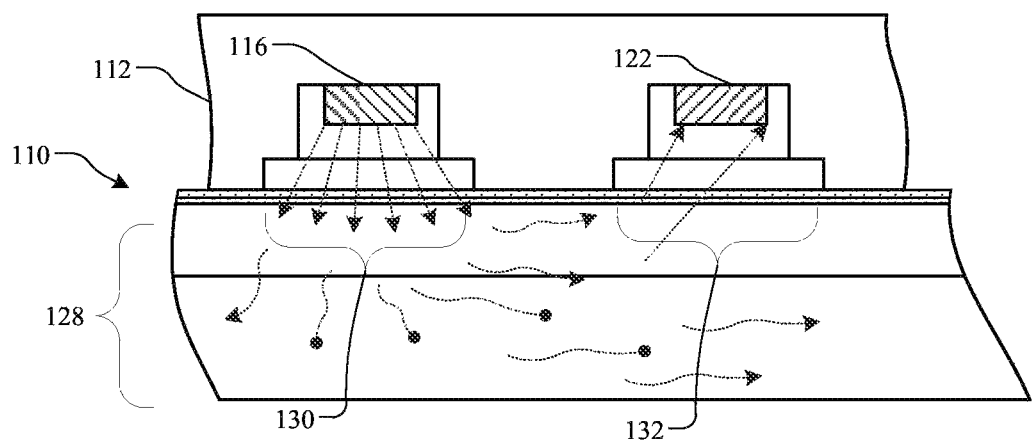
FIG. 2B depicts the detailed cross-section of FIG. 2A, showing a set of example light paths from a light source through a measurement site of a subject to an optical sensor of the optical sensing system.

FIG. 2B depicts a second cross-section like that of FIG. 2A, now showing a set of example light paths from a light source through a measurement site 110 of a subject to an optical sensor of the optical sensing system. As illustrated, light emitted from the light source 116 passes into an illumination area 130 of the measurement site 110, through an intermediate volume 128 of the measurement site 110, to a collection area 132 of the measurement site 110, and, thereafter, exits the collection area 132 where it may be collected by the optical sensor 122 and conveyed to the health monitoring device 102. In many embodiments, the subject may be a human user.

As illustrated, a portion of the light emitted from the light source 116 may not exit the intermediate volume 128 through the collection area 132. For example, some light may continue transmitting in a direction parallel to the length of the intermediate volume 128. In addition, some light can transmit in directions away from the collection area 132. In addition, some light can be absorbed within the intermediate volume collection area 132, depicted in FIG. 2B as point-terminated lines. Accordingly, the quantity of light received by the optical sensor 122 may be less than the quantity of light emitted by the light source 116.

Figure 3:
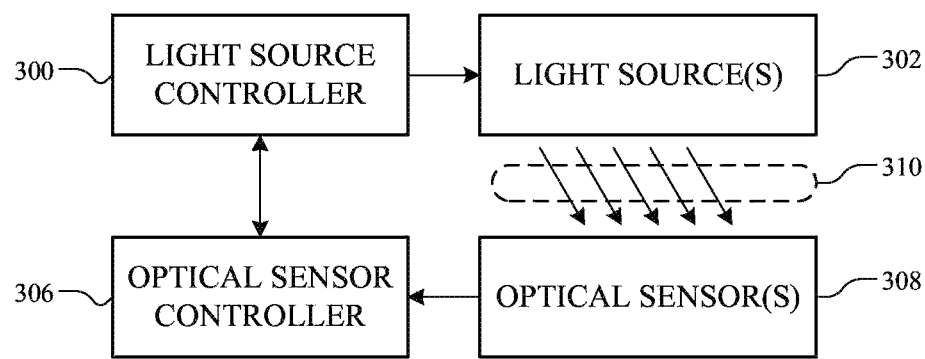
FIG. 3 depicts a simplified signal flow diagram of an optical sensing system.

FIG. 3 depicts a simplified signal flow diagram of an optical sensing system. An optical sensing system can include a light source controller 300 that is coupled to one or more light sources 302. The light source controlled 300 can be implemented as a microprocessor, integrated circuit, with discrete circuitry, or using any other suitable technique. The light source controller 300 can be configured to control the power state, brightness, and/or color of the light emitted by the one or more light sources 302. For example, in some embodiments the light source(s) 302 can include a light configured to emit green light and a second light configured to emit infrared light. In such an embodiment, the light source controller 300 can alternately illuminate the green light and the infrared light. In another example, the light source controller 300 can illuminate the green light and the infrared light at the same time.

The optical sensing system of FIG. 3 can also include an optical sensor controller 306 that is configured to receive output from the one or more optical sensors 308. The optical sensors 308 can receive light from the light source 302 that has reflected or transmitted through a measurement site 310 of a subject. In many embodiments, the subject may be a human user.

The optical sensor controller 306 can be implemented as a microprocessor, integrated circuit, with discrete circuitry, or using any other suitable technique. The optical sensor controller 306 can also be coupled to the light source controller 300. In many examples, the optical sensor controller 306 can use information provided by the light source controller 300. For example, in one embodiment, the light source controller 300 can inform the optical sensor controller 306 that the light source controller 300 is not illuminating any of the light sources 302. Alternatively, the light source controller 300 can inform the optical sensor controller 306 that the light source controller 300 is illuminating a particular light source 302.

In some embodiments described herein, the optical sensor controller 306 can implement one or more operations in an attempt to attenuate environmental noise. In one embodiment, the optical sensor controller 306 can implement a dark-channel subtraction operation. As described above, a dark-channel subtraction operation can take a sample output from an optical sensor 308 when the light source is not illuminated in order to determine the amount of ambient light received by the sensor when the light sources are "dark." Shortly thereafter, a light source 302 can be illuminated and another sample can be taken. Next, the "dark" sample can be subtracted from the "light" sample.

The optical sensor controller 306 can implement the dark-channel subtraction operation with assistance from the light source controller 300. For example, the light source controller 300 can inform the optical sensor controller 306 when light sources are on or off. In alternate embodiments, the optical sensor controller 306 can direct the light source controller 300 to turn particular light sources 302 on or off.

In further embodiments, the light source controller 300 and/or the optical sensor controller 306 can be implemented as software instructions to be executed by a processor associated with a health monitoring device.

Figure 4:
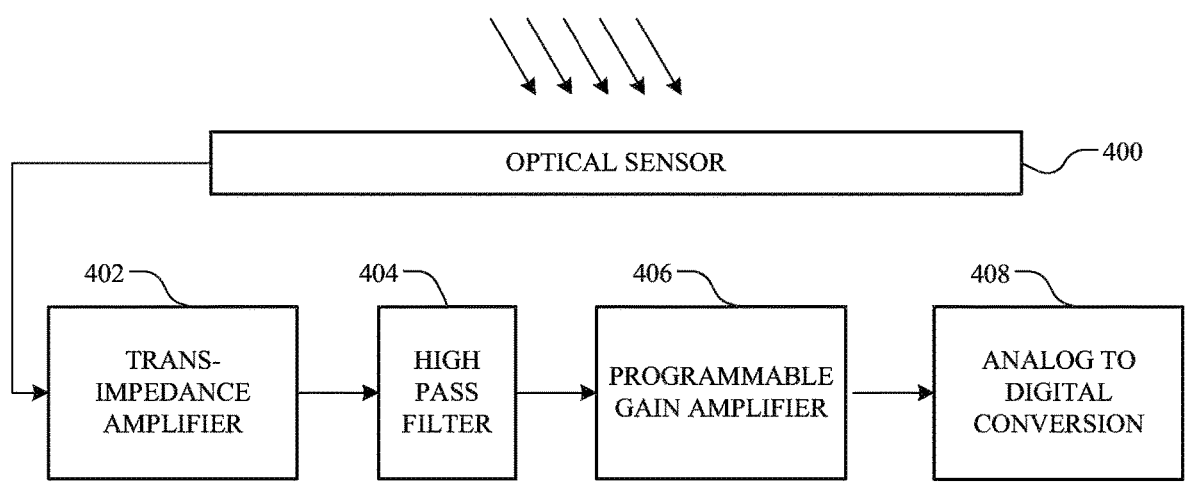
FIG. 4 depicts a simplified signal flow diagram of amplification and filtering stages of an optical sensing system.

FIG. 4 depicts a simplified signal flow diagram of amplification and filtering stages of an optical sensing system. In the illustrated embodiment, the optical sensor 400 can receive light. In many examples, the light may be transmitted from a light source associated with the optical sensing system, but, as noted above, additional environmental light can be received by the optical sensor as well.

After the light is received by the optical sensor 400, the optical sensor 400 may convert the light into analog electrical signals. In many examples, the optical sensor 400 can be a photodiode. Next, the analog electrical signal can be received by a transimpedance amplifier at 402. In many examples, a transimpedance amplifier can be suitable to convert the current output from a photodiode to a usable voltage. In such examples, measuring the current changes through a photodiode may be preferable to measuring the voltage changes across a photodiode because current may vary more linearly with changes in light than voltage. In one embodiment, the photodiode can be zero biased. In other examples the photodiode can be reverse biased.

After the analog electrical signal is amplified by the transimpedance amplifier 402, the amplified analog electrical signal can be passed through a high pass filter at 404. As noted with respect to embodiments described above, a high pass filter can be useful to remove low frequency components within the electrical signal that might otherwise interfere with detection of low frequency physiological parameters such as heart rate.

As noted above, the cutoff frequency of the high pass filter 404 can be selected to be below the frequency of modulation of light expected from the light source. For example, if the light source is modulating at 1 KHz, the cutoff frequency of the high pass filter can be 750 Hz. In other embodiments, the cutoff frequency can be closer or father away from the modulation frequency.

In other examples, the filter can be implemented as a band pass filter. For example, if the light source is modulating light at 1 KHz, a band pass filter can have a lower cutoff at 750 z and a high cutoff at 1.25 KHz. In other examples, different cutoff frequencies can be used.

In many examples, the filter can also remove direct current biases present within the signal.

After the signal is filtered by the high pass filter 404, it can be passed to a programmable gain amplifier at 406 and thereafter to an analog to digital converter at 408. The programmable gain amplifier 406 can increase the dynamic range of the optical sensor. For example, certain users may have darker skin than other users. Accordingly, the amount of light absorbed by the measurement site can vary from person to person. In these embodiments, the programmable gain amplifier 406 can be adjusted on a per-user basis in order to provide the maximum signal to the analog to digital converter 408.

In other examples, the gain of the programmable gain amplifier 406 can be based, at least in part, on feedback from the analog to digital converter 408. For example, if the analog to digital converter 408 determines that the average signal output from the programmable gain amplifier 406 is too low, then the analog to digital converter 408 can cause the programmable gain amplifier 406 to increase gain by a certain amount. In other examples, if the analog to digital converter 408 determines that the average signal output from the programmable gain amplifier 406 is too high (e.g., clipping is detected), then the analog to digital converter 408 can cause the programmable gain amplifier 406 to decrease gain by a certain amount.

Figure 5:
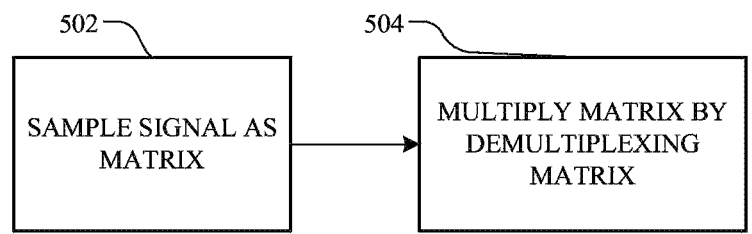
FIG. 5 depicts a simplified signal flow diagram of a demodulation stage of an optical sensing system.

FIG. 5 depicts a simplified signal flow diagram of a demodulation stage of an optical sensing system. In the illustrated embodiment, a digital signal can be received and sampled into a matrix at 502. Thereafter at 504, the matrix can be multiplied by a demodulation matrix in order to obtain a substantially noise-free measurement of the physiological parameters of a measurement site.

A demodulation matrix can be calculated in a number of ways. For example, in certain embodiments, a demodulation matrix can be fixed. In other embodiments, a different demodulation matrix can be selected depending upon particular environmental conditions. In still further embodiments, a plurality of demodulation matrices can be iterated through in order to determine which demodulation matrix obtains the highest quality output signal.

In still further embodiments, a demodulation matrix can be calculated dynamically and/or during a calibration procedure. For example, as with other embodiments described herein, an optical sensing system can have a plurality of light sources, a measurement site, and an optical sensor.

In many embodiments, the light sources can output modulated light. For example, if an embodiment is implemented with four light sources, a single light source can be illuminated at a time. Once all light sources have been illuminated, the cycle can repeat. In other words, the output of light from a light sensor may be periodic with period T, sampled for k periods. The function can be modeled as:

$$x(t)=x(t+kT) \qquad \text{Equation 1}$$

In one example, the function x(t) may be the light as it reaches the measurement site. In other words, light that has been affected by physiological parameters of the measurement site, but that is not yet accompanied or affected by environmental noise. As noted above, the light may pass through the measurement site and may be joined by other noise sources. In other words, the light can pass through a linear time invariant system having an unknown impulse. Such a function can be modeled as H(t). Accordingly, once the light reaches the optical sensor, it may have been affected by the linear time invariant system. In other words, the light that reaches the sensor y(t) can be modeled as the convolution of x(t)*H(t):

$$y(t) = \int_{-\infty}^{\infty} H(\tau) x(t+\tau) d\tau = y(t+kT) \quad \text{Equation 2}$$

However, as noted above, in some embodiments, multiple light sources can be used. Accordingly, the original signal x(t) can be represented by a sum of n individual signals, each having a unique scaling factor α associated with it:

$$x(t) = \Sigma_{i=1}^{n} \alpha_i(t) x_i(t) \quad \text{Equation 3}$$

Because light noise may not be modulated at the modulated frequency, the scaling factors may α vary and/or correspond to the physiological parameters of the measurement site.

In many embodiments, it can follow from Equation 3 that the scaling factors can pass through the linear time invariant system H(t), to be directly measured when measuring y(t):

$$y(t) = \Sigma_{i=1}^{n} \alpha_i(t) y_i(t) \quad \text{Equation 4}$$

In other words, the measured signal y(t), may be composed of a number of individual signals $y_i(t)$; once the individual signals $y_i(t)$ can be demultiplexed and demodulated, the individual scaling factors, and thus the physiological parameters of the measurement site, can be determined.

In certain embodiments, various assumptions can assist in demuxing and demodulating the signal y(t). For example, by turning on a single light source and/or turning of all light sources, the signal x(t) can be computationally simplified. Also, in embodiments directed to detecting low frequency physiological signals such as heart rate, it can be assumed that the scaling factors do not change between samples of particularly high sampling rates.

Also as noted above, dark-channel subtraction may be implemented while demodulating to attempt to remove as much noise as possible before further signal processing. For example, a demodulated signal $z_j(k)$ can be formed from synchronous samples of y(t) at individual time instances $\tau_j$. In sync with sampling, the light source can turn on and off at known rate. In this manner, time instances $\tau_j$ can fall immediately between dark periods of a light source. In other words, a dark sample can be taken at $\tau_j - \Delta_j$ and another dark sample can be taken at $\tau_j + \Delta_j$. Between the dark samples, at $\tau_j$, a "light" sample can be taken. The dark channel subtraction can be modeled as:

$$z_j(k) = y(t_0 + kT + \tau_j) - \frac{y(t_0 + kT + \tau_j - \Delta_j) + y(t_0 + kT + \tau_j + \Delta_j)}{2} \quad \text{Equation 5}$$

In many embodiments, the demodulated signal $z_j(k)$ can include m samples. In other words, Equation 5 can be defined from j=1 . . . m.

As noted above, individual light sources can be turned on or off. Accordingly, in some embodiments, one light source i may be turned on a time to simplify the calculation of demodulation. More specifically, a demodulated signal $z_j(k)$ that relates specifically to one light source i can be modeled as:

$$z_{j,i}(k) = \alpha_i(t) y_i(t) \quad \text{Equation 6}$$

Which in turn can be modeled as:

$$z_{j,i}(k) = \alpha_i(t_0 + kT + \tau_j) \omega_{j,i} \quad \text{Equation 7}$$

Where:

$$\omega_{j,i} = y(t_0 + kT + \tau_j) - \frac{y(t_0 + kT + \tau_j - \Delta_j) + y(t_0 + kT + \tau_j + \Delta_j)}{2} \quad \text{Equation 8}$$

In order to simplify the calculation, some embodiments can utilize the presumption that because the Equations 1-8 are time invariant, then $t_0=0$. In some embodiments, the simplified calculation can be modeled as:

$$z_{j,i}(k) = \alpha_i(kT + \tau_j) \omega_{j,i} \quad \text{Equation 9}$$

Where:

$$\omega_{j,i} = y(\tau_j) - \frac{y(\tau_j - \Delta_j) + y(\tau_j + \Delta_j)}{2} \quad \text{Equation 10}$$

Accordingly, in certain embodiments, the dark-channel subtraction demodulation operation can be accomplished by calculating $\omega_{j,i}$. In other words, because $z_{j,i}(k)$ is measureable, the only unknowns in Equation 9 are, generally speaking, $\omega_{j,i}$ and $\alpha_i(kT + \tau_j)$. However, after the demodulation process, one may appreciate that demultiplexing may still be required.

Accordingly, certain embodiments may attempt to estimate $\omega_{j,i}$. For example, all individual light sources i=1 . . . n can be demultiplexed as described above with respect to the examples of Equations 5-10. In such embodiments, an individual light source can be illuminated while all other light sources are turned off, and the light source can be sampled a certain number of times. As described above, each "sample" can actually constitute three samples; two "dark" samples can be averaged and subtracted from a single "light" sample. Once m samples are taken of the selected light source, the next light source can be selected.

For example, lights sources i=1 . . . n can be sampled with samples j=1 . . . m, and thus all measured results can be modeled as a matrix:

$$Z(k) = \begin{bmatrix} Z_{1,1} & \cdots & Z_{1,m} \\ \vdots & \ddots & \vdots \\ Z_{n,1} & \cdots & Z_{n,m} \end{bmatrix} \quad \text{Equation 11}$$

Correspondingly, the demodulation values can be modeled as a matrix:

$$W = \begin{bmatrix} \omega_{1,1} & \cdots & \omega_{1,m} \\ \vdots & \ddots & \vdots \\ \omega_{n,1} & \cdots & \omega_{n,m} \end{bmatrix} \quad \text{Equation 12}$$

One may note that the demodulation values does not vary with k. In addition, the scalar coefficients can be modeled as a matrix:

$$A(k) = \begin{bmatrix} \alpha_{1(kT)} & \cdots & 0 \\ \vdots & \ddots & \vdots \\ 0 & \cdots & \alpha_{n(kT)} \end{bmatrix} \qquad \text{Equation 13}$$

Alternatively, some embodiments can model the system as the matrix equation, presuming that W is full rank and that n=m:

$$Z(k)=A(k)W \qquad \text{Equation 14}$$

Thus, in order to calculate the scaling factors A(k), given only the measured values from the optical sensor, Z(k), some embodiments utilize the simplification:

$$A(k)=Z(k)W^{-1} \qquad \text{Equation 15}$$

In this configuration, the matrix $W^{-1}$ represents demultiplexing constants.

However, in many embodiments, Equation 15 is only useful once and unless the demultiplexing constants are known and/or estimated. Accordingly, in some embodiments, an initial matrix of $A_{init}$ can be supplied. For example, an identity matrix may be used in certain embodiments:

$$A_{init} = \begin{bmatrix} 1 & \cdots & 0 \\ \vdots & \ddots & \vdots \\ 0 & \cdots & 1 \end{bmatrix} \qquad \text{Equation 16}$$

In other embodiments, an initial matrix of $A_{init}$ can be supplied from the diagonal of the measured matrix Z(k). For example, an identity matrix may be used in certain embodiments:

$$A_{init} = \begin{bmatrix} Z_{1,1} & \cdots & 0 \\ \vdots & \ddots & \vdots \\ 0 & \cdots & Z_{n,m} \end{bmatrix} \qquad \text{Equation 17}$$

Thus, in some embodiments, by multiplying the matrix inverse of the measured values $Z(k)^{-1}$ with the initial matrix $A_{init}$, a first estimation of the demultiplexing constants $W^{-1}$ can be calculated. For example:

$$A_{init}Z(k)^{-1}=W^{-1} \qquad \text{Equation 18}$$

In some embodiments, the demultiplexing constants can be calculated and averaged with previous demultiplexing constants. After a sufficient number of calculations of the demultiplexing constants, returning to FIG. 5, a sampled signal matrix at 502 can be multiplied by a demultiplexing matrix at 504 to obtain scalar constants corresponding to physiological parameters of the measurement area.

Figure 6:
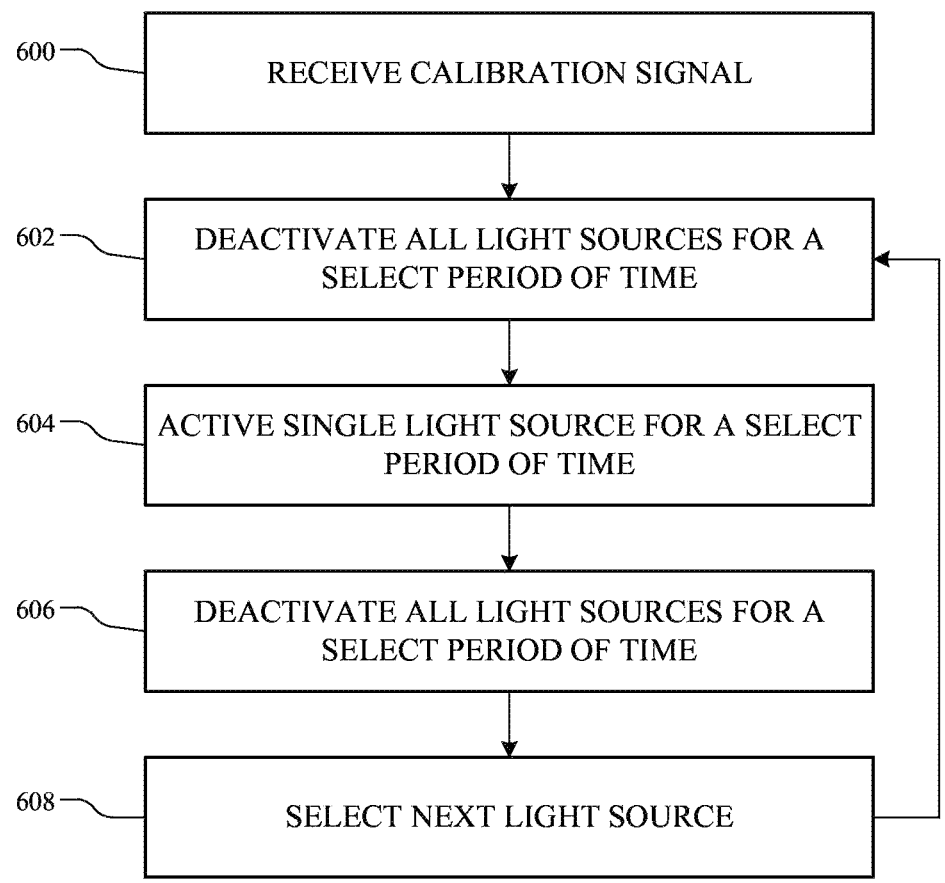
FIG. 6 depicts example operations of a method of calibrating an optical sensing system performed by a light source controller.

FIG. 6 depicts example operations of a method of calibrating an optical sensing system performed by a light source controller. The method can begin at operation 600 in which a light source controller receives a calibration signal. Next at 602, all lights controlled by the light source controller can be turned off for a selected period of time. In many examples, operation 602 may be a first "dark" sample collection period of a dark-channel subtraction process. Next at 604, one individual light can be turned on for a selected period of time. In many examples, operation 605 may be the "light" sample of a dark-channel subtraction process. Next at 606, all lights controlled by the light source controller can be turned off for another selected period of time. In many embodiments, operation 606 can be a second "dark" sample collection period of a dark-channel subtraction process. Lastly at operation 608, the method can cycle back to operation 602 after selecting the next light source to illuminate individually.

The order in which lights are illuminated can vary from embodiment to embodiment. For example, certain embodiments may illuminate adjacent lights sequentially. In other examples, a random or pseudorandom illumination pattern can be used.

Figure 7:
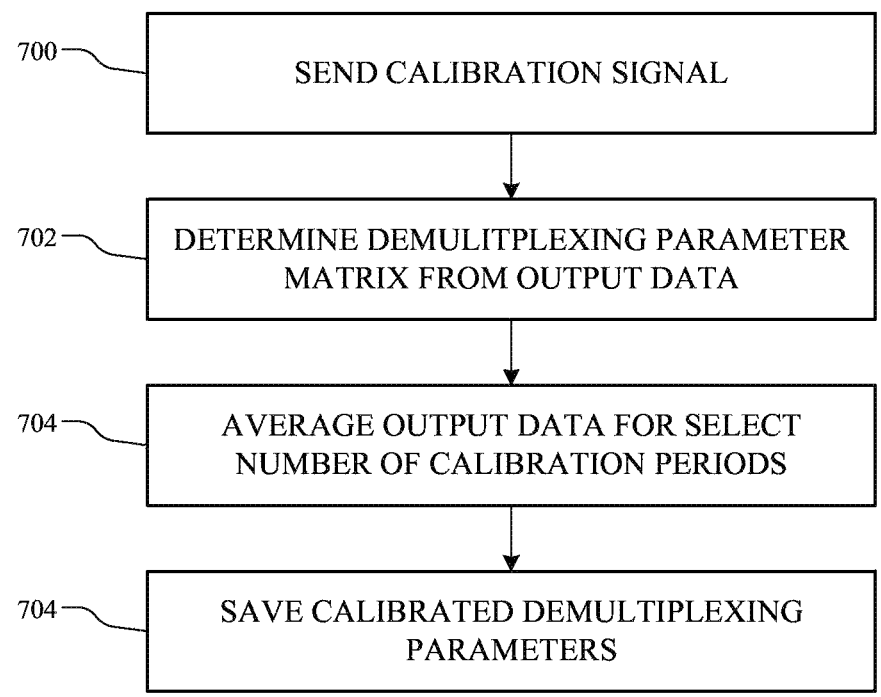
FIG. 7 depicts example operations of a method of calibrating an optical sensing system performed by an optical sensor controller.

FIG. 7 depicts example operations of a method of calibrating an optical sensing system performed by an optical sensor controller. The method can begin at operation 700 in which a calibration signal is sent by an optical sensor controller to a light source controller. Next at operation 702, a demultiplexing matrix can be determined and/or estimated. For example, as described with respect to FIG. 5. The method can continue to operation 704 at which a number of calculated demultiplexing matrices are calculated and averaged. The method can conclude at operation 706 during which the average demultiplexing matrix is saved for future use.

For example, a saved demultiplexing matrix can be used in conjunction with Equation 15, modified to account for all light sources being active:

$$[\alpha_1(kT) \ldots \alpha_n(kT)]=[z_1(kT) \ldots z_n(kT)]W^{-1} \qquad \text{Equation 19}$$

Many embodiments of the foregoing disclosure may include or may be described in relation to various methods of operation, use, manufacture, and so on. Notably, the operations of methods presented herein are meant only to be exemplary and, accordingly, are not necessarily exhaustive. For example an alternate operation order, or fewer or additional steps may be required or desired for particular embodiments.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not meant to be exhaustive or to limit the embodiments to the precise forms disclosed. It will be apparent to one of ordinary skill in the art that many modifications and variations are possible in view of the above teachings. In particular, any features described with respect to one embodiment may also be used in other embodiments, where compatible. Likewise, the features of the different embodiments may be exchanged, substituted, or omitted where compatible and appropriate.

We claim:

1. A biometric sensor within a housing of a wearable electronic device, the biometric sensor comprising:
    a plurality of emitters, each configured to transmit modulated light toward a measurement site of a subject through a first aperture in the housing;
    an optical sensor for receiving modulated light through a second aperture in the housing, the modulated light at least partially exiting the measurement site;
    a high pass filter to receive an output of the optical sensor, the high pass filter having a cutoff frequency above a frequency of a periodic optical property of the measurement site; and
    an analog to digital converter to receive an output of the high pass filter.

2. The biometric sensor of claim 1, wherein the cutoff frequency is greater than a low-frequency alias that results from dark-channel subtraction.

3. The biometric sensor of claim 1, wherein the high pass filter is configured to remove direct current bias in the output of the optical sensor.

4. The biometric sensor of claim 1, wherein a first emitter of the plurality of emitters is configured to transmit light within a first frequency band and a second emitter of the plurality of emitters is configured to transmit light within a second frequency band different from the first frequency band.

5. The biometric sensor of claim 4, wherein:
the first frequency band comprises green light; and
the second frequency band comprises infrared light.

6. The biometric sensor of claim 1, wherein a first emitter of the plurality of emitters is configured to transmit light at a first time and a second emitter of the plurality of emitters is configured to transmit light at a second time different from the first time.

7. The biometric sensor of claim 6, wherein the first emitter and the second emitter transmit light in sequence.

8. The biometric sensor of claim 1, further comprising a programmable gain amplifier in series between the high pass filter and the analog to digital converter.

9. The biometric sensor of claim 8, wherein a gain of the programmable gain amplifier is based, at least in part, on an optical property of the measurement site.

10. The biometric sensor of claim 8, wherein a gain of the programmable gain amplifier is based, at least in part, on an output from the analog to digital converter.

11. A biometric sensor within a housing of a wearable electronic device, the biometric sensor comprising:
a first emitter for transmitting modulated light in a first frequency band toward a measurement site of a subject through a first lens positioned in the housing;
a second emitter for transmitting modulated light in a second frequency band toward the measurement site through the first lens;
an optical sensor for receiving modulated light through a second lens positioned in the housing and offset from the first lens;
a first amplifier to receive an output of the optical sensor; and
a high pass filter to receive an output of the first amplifier, the high pass filter having a cutoff frequency above a frequency of a periodic optical property of the measurement site;
a second amplifier to receive an output of the high pass filter; and
an analog to digital converter to receive an output of the second amplifier.

12. The biometric sensor of claim 11, wherein the first amplifier is a transimpedance amplifier and the second amplifier is a programmable gain amplifier.

13. The biometric sensor of claim 12, wherein a gain of the programmable gain amplifier is increased or decreased based on feedback from the analog to digital converter.

14. The biometric sensor of claim 11, further comprising a demodulation stage to receive an output of the analog to digital converter.

15. The biometric sensor of claim 14, wherein the demodulation stage is configured to:
sample data output from the analog to digital converter into a matrix; and
multiply the matrix by a demodulation matrix to demodulate the received modulated light.

16. The biometric sensor of claim 15, wherein the demodulation matrix is a first demodulation matrix and the demodulation stage comprise a plurality of demodulation matrices.

17. The biometric sensor of claim 16, wherein the demodulation stage is configured to iterate through each demodulation matrix of the plurality of demodulation matrices to determine which demodulation matrix is associated with a highest quality output signal.

18. A biometric sensor within a housing of a wearable electronic device, the biometric sensor comprising:
an emitter for transmitting modulated light within a frequency band toward a measurement site of a subject through a first aperture in a convex portion of the housing;
an optical sensor for receiving modulated light through a second aperture in the convex portion of the housing, the second aperture opposite the first aperture such that an apex of the convex portion of the housing is between the first aperture and the second aperture;
a high pass filter to receive an output of the optical sensor, the high pass filter having a cutoff frequency above a frequency of a periodic optical property of the measurement site; and
an analog to digital converter to receive an output of the high pass filter.

19. The biometric sensor of claim 18, wherein the optical sensor is configured to obtain at least one dark sample before each sample of the modulated light.

\* \* \* \* \*